United States Patent [19]

Armstrong et al.

[11] 4,081,527

[45] * Mar. 28, 1978

[54] CHLORTETRACYCLINE COMPOSITIONS

[75] Inventors: William W. Armstrong, Mill Neck, N.Y.; Saurabhkumar J. Desai, Groton, Conn.

[73] Assignee: Pfizer Inc., New York, N.Y.

[*] Notice: The portion of the term of this patent subsequent to Apr. 19, 1994, has been disclaimed.

[21] Appl. No.: 748,175

[22] Filed: Dec. 7, 1976

[51] Int. Cl.² .................. A61K 31/79; A61K 31/65
[52] U.S. Cl. .................................... 424/80; 424/227
[58] Field of Search ..................... 424/227, 80

[56] References Cited

U.S. PATENT DOCUMENTS

| | | | |
|---|---|---|---|
| 2,987,437 | 6/1961 | Hessel | 424/227 |
| 3,062,717 | 11/1962 | Hammer | 424/227 |
| 3,932,653 | 1/1976 | Stoughton | 424/285 |
| 3,957,994 | 5/1976 | Schroer | 424/253 |
| 3,969,516 | 7/1976 | Stoughton | 424/181 |

FOREIGN PATENT DOCUMENTS

| | | |
|---|---|---|
| 1,053,736 | 3/1959 | Germany. |
| 1,091,287 | 4/1961 | Germany. |
| 2,557,431 | 6/1976 | Germany. |
| 802,111 | 9/1956 | United Kingdom. |
| 805,026 | 2/1957 | United Kingdom. |

OTHER PUBLICATIONS

Japanese Patent Appln. Publicat. No. Sho 47–303 (Jan. 6, 1972).
Japanese Patent Appln. Publicat. No. Sho 43–1758 (Jan. 22, 1968).
Gans & Higuchi – J. Pharm. Sci., vol. 46, (1957) p. 458.

*Primary Examiner*—Sam Rosen
*Attorney, Agent, or Firm*—Francis X. Murphy; Charles J. Knuthy; Allen J. Spiegel

[57] ABSTRACT

Aqueous solutions of chlortetracycline or salts thereof, a pharmaceutically acceptable calcium compound and 2-pyrrolidone as a co-solvent, said solution having a pH of 8 to 10 and being useful as an injectable composition combining low viscosity, high potency, good clarity and good stability.

8 Claims, No Drawings

CHLORTETRACYCLINE COMPOSITIONS

BACKGROUND OF THE INVENTION

This invention relates to antibiotic compositions suitable for pharmaceutical use. More particularly, it relates to chlortetracycline solutions containing 2-pyrrolidone.

Previous efforts made to prepare high concentration chlortetracycline solutions have been unsuccessful. This is of particular importance in the case of veterinary parenteral compositions for administration to large animals.

Japanese Patent Publication No. Sho 47-303 discloses stable aqueous solutions of p-biphenylmethyl (dl-tropyl-α-tropinium) bromide, 2.5%, in which 2-pyrrolidone is present in a concentration of 20%. The use of polyvinylpyrrolidone at a concentration of 30% is also disclosed. The pH of these solutions is less than 7, the preferred range being 3-4.

Japanese Patent Publication No. Sho 43-1758 discloses insecticidal solutions containing hexachlorcyclohexane in alcohol and 2-pyrrolidone as solvents. The use of N-methyl pyrrolidone as a co-solvent is also disclosed.

British Patent Specification No. 802,111 discloses pesticidal compositions containing 2-pyrrolidone or N-methyl pyrrolidone as solvents for DDT, dieldrin, aldrin and similar insecticides. The use of 67-82% of 2-pyrrolidone is exemplified.

British Patent Specification No. 805,026 discloses the use of N-methyl pyrrolidone in concentrations of 40% as a solvent for various medicaments intended for parenteral administration, such as chloramphenicol, N,N'-dibenzyl ethylenediamine-dipenicillin G and procaine penicillin.

U.S. Pat. No. 2,987,437 discloses nematocidal compositions of 3,4-dichlorotetrahydrothiophene, 1,1-dioxide in 2-pyrrolidone.

German Pat. No. 1,091,287 discloses stable aqueous solutions of tyrothricin 0.25% or subtilin 0.2% for nasal or otic use prepared with the aid of pyrrolidione and/or polyvinylpyrrolidone as solubilizers. Pyrrolidone is used in a concentration of 0.5% and polyvinylpyrrolidone can be used up to 10%.

U.S. Pat. No. 3,062,717 discloses aqueous parenteral solutions of tetracycline calcium complexes containing 35-80% of an amide of acetic or lactic acid, such as N,N-dimethylacetamide or N-(β-hydroxyethyl) lactamide, at a pH of 7 to 9.5. Concentrations of 10 to 100 mg/ml are disclosed.

J. Pharm. Sci. 46, p. 458 (1957) discloses that oxytetracycline forms soluble complexes with N-methyl pyrrolidone in aqueous solution. The degree of interaction is limited by pH and solubility considerations.

U.S. Patent Application Ser. No. 646,295, now U.S. Pat. No. 4,018,889 discloses oxytetracycline solutions containing from about 1 to 40 percent oxytetracycline in an aqueous vehicle containing from about 10 to 50 percent by weight of 2-pyrrolidone, about 0.8 to 1.3 molar proportions of a pharmaceutically acceptable magnesium compound soluble in the said solution, said solution having a pH value in the range of from about 7.5 to 9.5.

SUMMARY OF THE INVENTION

It has now been found that stable high potency solutions of chlortetracycline can be provided by means of a novel pharmaceutical composition comprising an aqueous solution of from about 5 to 20% by weight of an antibiotic compound selected from chlortetracycline and the pharmaceutically acceptable acid addition salts thereof, about 2 to 4 molar proportions based on said antibiotic of a pharmaceutically acceptable calcium compound soluble in said solution, and from about 50 to 70% by weight of 2-pyrrolidone, said composition having a pH value in the range of from about 8 to 10.

DETAILED DESCRIPTION OF THE INVENTION

Chlortetracycline, the therapeutically-active component of this invention, is a widely used tetracycline-type antibiotic. It is particularly described in U.S. Pat. No. 2,482,055. An effective concentration range for chlortetracycline in the solutions of this invention is generally from about 5 to 20% by weight of the total in the form of the free base or a pharmaceutically acceptable acid addition salt. The preferred form is the acid addition salt with the preferred concentration being from about 10 to 20% by weight, with the especially preferred concentration being from about 10 to 15% by weight.

Examples of suitable chlortetracycline acid addition salts which can be used include such pharmaceutically acceptable acid addition salts as hydrochloride, hydrobromide and sulfate. However, the preferred acid addition salt is chlortetracycline hydrochloride.

Calcium ions combine with chlortetracycline in solution to form calcium-tetracycline chelates. Calcium chloride is a convenient and preferred source of calcium ions, but other compounds useful for the purpose of this invention include calcium oxide, calcium acetate and calcium sulfate. The molar ratio of calcium to chlortetracycline in these compositions is about from 2 to 4. This ratio is advisable to produce clear stable solutions.

2-Pyrrolidone is present as a co-solvent in a concentration of from about 50 to 70%, and preferably from about 60 to 70% based on the total weight of the composition. 2-Pyrrolidone is also known as 2-pyrrolidinone, 2-oxopyrrolidine, α-pyrrolidone and 2-ketopyrrolidine. It has an oral $LD_{50}$ of 8 gm/kg in rats and 3.8 gm/kg by intraperitoneal injection in mice. Its use allows for minimum volume per dose and excellent satisfactory due to low viscosity of the resultant composition.

As an optional ingredient polyvinylpyrrolidone may also be present in a concentration of from about 1 to 7% by weight. The polyvinylpyrrolidone preferred for this invention is one having an average molecular weight of between about 5,000 and 100,000 (K-12 to 30) and especially between about 10,000 and 17,000 (K - 17). It is present in part as a cosolubilizer and may improve tissue toleration.

The stability of these solutions for therapeutic administration is still further enchanced by the use of antioxidants such as sodium or magnesium formaldehyde sulfoxylate and monothioglycerol at levels of from about 0.01 to 1.0% by weight.

The pH value is adjusted if necessary to pH 8 to 10. The preferred range is pH 8.5 to 9.5. The pH can be adjusted with an organic base such as monoethanolamine or with a pharmaceutically acceptable acid, such as hydrochloric acid.

The compositions of this invention are readily prepared by mixing the calcium compound with the 2-pyrrolidone and water at about 50° C and slowly adding the chlortetracycline antibiotic with stirring and adjusting the pH to the desired range. If polyvinylpyrrolidone is to be included it is added to the 2-pyrrolidone and water before the addition of the calcium compound as previously described.

These compositions are also easy to syringe over a wide temperature range and are satisfactory from a physical and chemical stability standpoint.

The use of these high potency chlortetracycline compositions enables a reduction of the number of injections that must be administered to large animals, such as steers, in order to receive an effective dose.

The primary application is as a parenteral composition but the new compositions can also be used for topical or oral application.

EXAMPLE 1

The following solution containing 100 mg/ml of chlortetracycline hydrochloride activity was prepared.

|  | gm/100 ml |
| --- | --- |
| Chlortetracycline hydrochloride (based on a chlortetracycline hydrochloride potency of 950γ/mg plus a 5% overage) | 11.053 |
| Calcium chloride | 4.96 |
| 2-Pyrrolidone | 60.00 |
| Monothioglycerol | 1.00 |
| Monoethanolamine, to adjust pH to 8.8 | |
| Water q.s. to | 100 ml |

The 2-pyrrolidone was mixed with water. The solution was heated to about 50° C. and the monothioglycerol was added and dissolved with stirring. The calcium chloride was then slurried with the solution. The chlortetracycline hydrochloride was slowly added with stirring and the pH raised with monoethanolamine until solution resulted. The solution was allowed to cool to room temperature and the pH adjusted to 8.8 with monoethanolamine. The solution was then brought up to volume with water.

Solutions comparable to the above were also made by adjusting the pH to 8.0 and 9.5 respectively.

EXAMPLE 2

The following solution containing 100 mg/ml of chlortetracycline hydrochloride activity was prepared using the procedure described in Example 1.

|  | gm/100 ml |
| --- | --- |
| Chlortetracycline hydrochloride (based on a chlortetracycline hydrochloride potency of 950γ/mg plus a 5% overage) | 11.053 |
| Calcium chloride | 9.92 |
| 2-Pyrrolidone | 60.00 |
| Monothioglycerol | 1.00 |
| Monoethanolamine, to adjust pH to 8.8 | |
| Water q.s. to | 100 ml |

Solutions comparable to the above were also made by adjusting the pH to 8.0 and 9.5 respectively.

EXAMPLE 3

The following solution containing 50 mg/ml of chlortetracycline hydrochloride activity was prepared.

|  | gm/100 ml |
| --- | --- |
| Chlortetracycline hydrochloride (based on a chlortetracycline hydrochloride potency of 950γ/mg plus a 5% overage) | 5.527 |
| Calcium chloride | 2.48 |
| 2-Pgyrrolidone | 50.00 |
| Polvinylpyrrolidone | 5.00 |
| Monothioglycerol | 1.00 |
| Monoethanolamine, to adjust pH to 8.8 | |
| Water q.s. to | 100 ml |

The 2-pyrrolidone was mixed with water. Polyvinylpyrrolidone was then added with stirring until dissolved. The procedure described in Example 1 was then followed.

Solutions comparable to the above were also made by adjusting the pH to 8.0 and 9.5 respectively.

EXAMPLE 4

The following solution containing 200 mg/ml of chlortetracycline hydrochloride activity was prepared using the procedure described in Example 1.

|  | gm/100 ml |
| --- | --- |
| Chlortetracycline hydrochloride (based on a chlortetracycline hydrochloride potency of 950γ/mg plus a 5% overage) | 22.106 |
| Calcium chloride | 9.92 |
| 2-Pyrrolidone | 60.00 |
| Monothioglycerol | 1.00 |
| Monoethanolamine, to adjust pH to 8.8 | |
| Water q.s. to | 100 ml |

Solutions comparable to the above were also made by adjusting the pH to 8.0 and 9.5 respectively.

EXAMPLE 5

The following solution containing 100 mg/ml of chlortetracycline hydrochloride activity was prepared using the procedure described in Example 1.

|  | gm/100 ml |
| --- | --- |
| Chlortetracycline hydrochloride (based on a chlortetracycline hydrochloride potency of 950γ/mg plus a 5% overage) | 11.053 |
| Calcium chloride | 4.96 |
| 2-Pyrrolidone | 70.00 |
| Monothioglycerol | 1.00 |
| Monoethanolamine, to adjust pH to 8.8 | |
| Water q.s. to | 100 ml |

Solutions comparable to the above were also made by adjusting the pH to 8.0 and 9.5 respectively.

EXAMPLE 6

The following solution containing 100 mg/ml of chlortetracycline hydrochloride activity was prepared using the procedure described in Example 3.

|  | gm/100 ml |
| --- | --- |
| Chlortetracycline hydrochloride (based on a chlortetracycline hydrochloride potency of 950γ/mg plus a 5% overage) | 11.053 |
| Calcium chloride | 4.96 |
| 2-Pyrrolidone | 60.00 |
| Polyvinylpyrrolidone | 5.00 |
| Monothioglycerol | 1.00 |
| Monoethanolamine, to adjust pH to 8.8 | |
| Water q.s. to | 100 ml |

Solutions comparable to the above were also made by adjusting the pH to 8.0 and 9.5 respectively.

What is claimed is:

1. A chlortetracycline composition comprising an aqueous solution of from about 5 to 20% by weight of an antibiotic compound selected from the group consisting of chlortetracycline and the pharmaceutically acceptable acid addition salts thereof, from about 2 to 4 molar proportions based on said antibiotic of a pharmaceutically acceptable calcium compound soluble in said solution, and from about 50 to 70% by weight of 2-pyrrolidone, said composition having a pH value in the range of from about 8 to 10.

2. A composition as claimed in claim 1 wherein said antibiotic compound is chlortetracycline hydrochloride.

3. A composition as claimed in claim 1 wherein said calcium compound is introduced in the form of calcium chloride.

4. A composition of claim 1 wherein polyvinylpyrrolidone having an average molecular weight of between about 5,000 and 100,000 is also present in a concentration of from about 1 to 7% by weight of the total.

5. A composition as claimed in claim 1 wherein said antibiotic compound is present at a level of from about 10 to 20% by weight.

6. A composition as claimed in claim 1 wherein said antibiotic compound is present at a level of from about 10 to 15% by weight.

7. A composition as claimed in claim 1 having a pH value of from about 8.5 to 9.5.

8. A chlortetracycline composition comprising an aqueous solution of from about 10 to 15% by weight of chlortetracycline, from about 2 to 4 molar proportions based on chlortetracycline of a pharmaceutically acceptable calcium compound soluble in said solution, from about 60 to 70% by weight of 2-pyrrolidone and from about 1 to 7% by weight of polyvinylpyrrolidone, said composition having a pH value in the range of from about 8.5 to 9.5.

* * * * *